(12) United States Patent
Swenson et al.

(10) Patent No.: US 12,257,439 B2
(45) Date of Patent: *Mar. 25, 2025

(54) LEADLESS CARDIAC PACEMAKER DEVICE CONFIGURED TO PROVIDE INTRA-CARDIAC PACING

(71) Applicant: BIOTRONIK SE & Co. KG, Berlin (DE)

(72) Inventors: Kurt Swenson, Dayton, OR (US); Shayan Guhaniyogi, Portland, OR (US); Ravi Kiran Kondama Reddy, Portland, OR (US); Christopher Jones, Oregon City, OR (US); Madeline Anne Midgett, Portland, OR (US); R. Hollis Whittington, Portland, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 217 days.

This patent is subject to a terminal disclaimer.

(21) Appl. No.: 17/980,759

(22) Filed: Nov. 4, 2022

(65) Prior Publication Data

US 2023/0058678 A1    Feb. 23, 2023

Related U.S. Application Data

(63) Continuation of application No. 17/117,434, filed on Dec. 10, 2020, now Pat. No. 11,529,521.
(Continued)

(51) Int. Cl.
*A61N 1/365* (2006.01)
*A61N 1/05* (2006.01)
(Continued)

(52) U.S. Cl.
CPC .............. *A61N 1/365* (2013.01); *A61N 1/056* (2013.01); *A61N 1/3682* (2013.01);
(Continued)

(58) Field of Classification Search
CPC ...... A61N 1/365; A61N 1/056; A61N 1/3705; A61N 1/37512; A61N 1/3756; A61N 1/3688; A61N 1/3682
See application file for complete search history.

(56) References Cited

U.S. PATENT DOCUMENTS

| | | |
|---|---|---|
| 2004/0064160 A1 | 4/2004 | Hettrick et al. |
| 2016/0067487 A1 | 3/2016 | Demmer et al. |
| (Continued) | | |

FOREIGN PATENT DOCUMENTS

| | | |
|---|---|---|
| EP | 2042087 A1 | 4/2009 |
| EP | 3218049 B1 | 4/2018 |
| WO | 2010088040 A1 | 8/2010 |

OTHER PUBLICATIONS

European Search Report and Annex to the European Search Report on European Patent Application No. EP 20 15 3186.0, dated Jul. 31, 2020 (7 pages).

*Primary Examiner* — Brian T Gedeon
(74) *Attorney, Agent, or Firm* — Buchanan Ingersoll & Rooney PC

(57) ABSTRACT

A leadless pacemaker device configured to provide for an intra-cardiac pacing, including: processing circuitry configured to generate ventricular pacing signals for stimulating ventricular tissue, and a reception device for receiving a sensing signal indicative of an atrial activity, wherein the processing circuitry is configured to detect an atrial event derived from said sensing signal, wherein the atrial event is a valid atrial sense event, where a series of atrial events lie within a range for a normal atrial rate, and/or when the atrial rate variability is within a certain range indicating a regular atrial rhythm, wherein in case a valid atrial sense event is detected, the processing circuitry is further configured to: determine ventricular pacing events according to atrial events, calculate ventricular-atrial time delays, determine a (Continued)

correction value based a measured time delay and the calculated time delay, and adjust the ventricular pacing timing based on the correction value.

14 Claims, 7 Drawing Sheets

Related U.S. Application Data

(60) Provisional application No. 62/948,854, filed on Dec. 17, 2019.

(51) Int. Cl.
    *A61N 1/368*     (2006.01)
    *A61N 1/37*     (2006.01)
    *A61N 1/375*     (2006.01)

(52) U.S. Cl.
    CPC ....... *A61N 1/3706* (2013.01); *A61N 1/37512* (2017.08); *A61N 1/3756* (2013.01)

(56) References Cited

U.S. PATENT DOCUMENTS

| | | |
|---|---|---|
| 2018/0021581 A1 | 1/2018 | An et al. |
| 2018/0028814 A1 | 2/2018 | Ghosh |
| 2019/0308022 A1 | 10/2019 | Demmer et al. |

LEADLESS CARDIAC PACEMAKER DEVICE CONFIGURED TO PROVIDE INTRA-CARDIAC PACING

CROSS-REFERENCE TO RELATED APPLICATIONS

This patent application is a Continuation Application of U.S. application Ser. No. 17/117,434, filed on Dec. 10, 2020, which claims the benefit of and priority to U.S. Provisional Patent Application No. 62/948,854, filed on Dec. 17, 2019, the entire disclosures of which is hereby incorporated by reference herein in their entireties.

TECHNICAL FIELD

The instant invention generally relates to a leadless cardiac pacemaker device for providing an intra-cardiac pacing, in particular a ventricular pacing.

BACKGROUND

In recent years, leadless pacemakers have received increasing attention. Leadless pacemakers, in contrast to pacemakers implanted subcutaneously using leads extending transvenously into the heart, avoid leads in that the pacemaker device itself is implanted into the heart, the pacemaker having the shape of a capsule for implantation into cardiac tissue, in particular the right ventricular wall of the right ventricle. Such leadless pacemakers exhibit the inherent advantage of not using leads, which can reduce risks for the patient involved with leads transvenously accessing the heart, such as the risk of pneumothorax, lead dislodgement, cardiac perforation, venous thrombosis and the like.

Leadless pacemakers may specifically be designed for implantation in the right ventricle and, in this case, during implant are placed in or on the right ventricular wall. A ventricular pacing may for example be indicated in case a dysfunction at the AV node occurs, but the sinus node function is intact and appropriate. In such a case in particular a so-called VDD pacing may be desired, involving a ventricular pacing with atrial tracking and hence requiring a sensing of atrial activity in order to pace at the ventricle based on intrinsic atrial contractions.

A pacing using atrial tracking is in particular motivated by patient hemodynamic benefits of atrioventricular (AV) synchrony by utilizing an appropriate sinus node function to trigger ventricular pacing, potentially allowing to maximize ventricular preload, to limit AV valve regurgitation, to maintain low mean atrial pressure, and to regulate autonomic and neurohumoral reflexes.

Publications have explored solutions to use modalities to detect mechanical events of atrial contractions, including the sensing of motion, sound and pressure. For example, U.S. Publication No. 2018/0021581 A1 discloses a leadless cardiac pacemaker including a pressure sensor and/or an accelerometer to determine an atrial contraction timing. As mechanical events generally exhibit a small signal volume, signal detection based on mechanical events, for example motion, sound or pressure, may be difficult to sense, in particular when the leadless pacemaker device is placed in the ventricle and hence rather far removed from the atrium of which contractions shall be sensed. In addition, wall motion and movement of blood generated by atrial contractions may not be directly translated to the ventricle, and cardiac hemodynamic signals, such as motion, heart sounds and pressure, are likely affected by external factors such as posture and patient activity.

European Patent No. 3 218 049 B1 describes a leadless pacemaker device that is configured for implantation in a ventricle of a heart of a patient and is configured to switch from an atrio-ventricular synchronous pacing mode to an asynchronous pacing mode in response to detection of one or more atrial undersensing events.

U.S. Publication No. 2018/0028814 A1 discloses an implantable medical device system operating in an atrial synchronized ventricular pacing mode and switching to an atrial asynchronous pacing mode when pacing mode switching criteria are met. A control circuit of the system detects a cycle length change between two atrial cycle lengths determined from a cardiac signal that includes far-field atrial triggering events. If the cycle length change is greater than a change threshold, the control circuit determines if the pacing mode switching criteria are satisfied subsequent to detecting the cycle length change.

Generally, if a competent sinus rhythm is available, it is assumed to be preferable to use the sinus rhythm to control a ventricular pacing rate rather than pacing at the ventricle using a rate response mechanism, such rate response mechanism generally causing an adaption of the pacing rate in dependence of personal activity of a patient (for example according to an accelerometer reading), such that the pacing rate is adapted dependent on whether the patient for example sleeps or is physically active or stressed. In times, however, where no sinus rhythm is available, due to for example an undersensing or an incompetent sinus, or when higher rate atrial arrhythmias are present, a pacing according to the sinus rhythm is no longer suitable, such that another pacing strategy, such as a pacing according to a rate response mechanism, is to be chosen.

Hence, at different times and conditions different pacing modes may have to be applied, making a switching between different modes necessary.

The present invention is directed toward overcoming one or more of the above-mentioned problems, though not necessarily limited to embodiments that do.

SUMMARY

It is an object to provide a leadless pacemaker device and a method for operating a leadless pacemaker device allowing, in particular, for a sensible switching between different pacing modes, in particular to adapt a ventricular pacing to a detected atrial sense rate.

Such desires are addressed by a leadless cardiac pacemaker device configured to provide for an intra-cardiac pacing and having the features of claim 1.

In an aspect of the present invention, a pacemaker device configured to provide for an intra-cardiac pacing, the leadless pacemaker device comprising:
 a processing circuitry configured to generate ventricular pacing signals for stimulating ventricular tissue, and
 a reception device for receiving a sensing signal indicative of an atrial activity, wherein the processing circuitry is configured to determine an atrial sense rate of atrial events derived from said sensing signal,
 wherein in case a valid atrial sense rate is determined, the processing circuitry is further configured to:
  determine a ventricular pacing rate according to the atrial sense rate based on a calculated atrial-ventricular (AV) delay, Generating at least one ventricular pacing signal at the ventricular pacing rate, determine a calculated ventricular-atrial delay ($VA_{calc}$) indicative of a time delay at which an atrial event (As) is predicted to occur following a prior ventricular event (Vs), measure a true occurrence of a time delay at which an atrial event (As) occurs following a prior ventricular event (Vs) ($VA_{true}$) and determine a correction value (CV) based on a timing relation between $VA_{true}$ and the calculated ventricular-atrial delay ($VA_{calc}$), and adjust said ventricular pacing rate based on the correction value (CV).

For instance, whether an atrial sense rate is valid can be identified according to the atrial rate and/or the atrial rate variability. In a first example, a valid atrial sense rate is determined when the atrial sense rate derived from said sensing signal lies within a range for a normal atrial rate. For an adult at rest, the normal atrial rate ranges from 60 to 100 bpm, higher during exercise. However, the range may deviate according to factors individual for the patient (age, diseases, medication, fitness level etc.). According to an embodiment, a valid atrial sense rate is determined when the atrial rate variability is within a certain range indicating a regular atrial rhythm. The variability of the atrial rhythm can be determined via the difference of time intervals between successive atrial events.

According to an embodiment, the processing circuitry is configured to determine a ventricular pacing rate based on a calculated ventricular pacing rate in case no valid atrial sense rate is determined.

According to an embodiment, an atrial sense rate is not valid if the atrial sense rate is outside the range of a normal atrial rate, or if the atrial rate variability is outside the range of a regular atrial rhythm. Alternatively, an atrial sense rate is not valid when no atrial events are received via the reception device, or when the noise level of the sensing signal is too high, or when atrial sensing/detection of the leadless pacemaker device is inhibited.

In one aspect, a leadless pacemaker device configured to provide for an intra-cardiac pacing comprises a processing circuitry configured to generate ventricular pacing signals for stimulating ventricular activity at a ventricular pacing rate, and a reception device for receiving a sensing signal indicative of an atrial activity, wherein the processing circuitry is configured to determine an atrial sense rate of atrial events derived from said sensing signal, wherein the processing circuitry is further configured to determine a correction value based on a difference between said ventricular pacing rate and said atrial a sensing rate and to adjust said ventricular pacing rate based on the correction value.

The leadless pacemaker device is configured to generate and emit pacing signals, the leadless pacemaker device being located in the right or left ventricle such that at least one pacing electrode is in electrical contact with cardiac tissue for injecting stimulation energy into cardiac tissue. Ventricular pacing signals are generally generated at a ventricular pacing rate, wherein the ventricular pacing rate is adaptive based on whether an atrial sense rate can be determined from a sensing signal received via the reception device or not.

Herein, in case an atrial sense rate—which is indicative of a timing between atrial events derived from the sensing signal picked up by means of the reception device—becomes available and suitable for a pacing, the ventricular pacing rate is adapted based on a difference between the ventricular pacing rate (as it has been used prior to picking up an atrial sense rate suitable for pacing) and the now detected atrial sense rate. Based on the difference between the ventricular pacing rate and the atrial sense rate a correction value is determined, and based on the correction value the ventricular pacing rate is adjusted.

By applying the correction value, in particular, the ventricular pacing rate is progressively adapted to come into synchrony with the atrial sense rate. The ventricular pacing rate hence is not promptly switched to match the detected atrial sense rate, but is progressively adjusted so that it approaches and converges towards the atrial sense rate. Once an atrial sense rate becomes available and usable for a pacing strategy, hence a progressive adjustment of the ventricular pacing rate is initiated in order to bring the ventricular pacing rate into synchrony with the atrial sense rate.

By applying such correction value an adjustment similar to a phase-locked loop (PLL) mechanism is applied to progressively adjust the ventricular pacing rate to an atrial sense rate in case an atrial sense rate becomes available from the sense reception signal and is suitable for pacing. By means of such phase-locked loop mechanism the correction value is used to progressively adjust the ventricular pacing rate in order to adapt the ventricular pacing rate until its phase is synchronized with the atrial sense rate (while taking an offset determined by the atrioventricular (AV) delay into account), the correction value being adapted in a feedback loop until the phase of the ventricular pacing rate is locked to the phase of the atrial sense rate.

In one embodiment, the processing circuitry is configured to determine an atrial interval indicative of a time interval between two successive atrial events. From the atrial sensing signal picked up by means of the reception device, atrial events indicative of atrial activity due to atrial contractions are determined, the atrial interval indicating the time between two successive atrial events. Generally, the ventricular interval, i.e., the interval between two successive ventricular pacing signals or intrinsic sense events, should match the atrial interval, the atrial sense rate being the inverse of the atrial interval and defining a quantity to which the ventricular pacing rate should be adapted for providing for an atrioventricular synchronous pacing operation.

The processing circuitry may, in one embodiment, be configured to determine a calculated ventricular-atrial delay indicative of a time delay at which an atrial event is predicted to occur following a prior ventricular pacing or sense event. The ventricular-atrial delay herein may for example be determined from a calculated atrial-ventricular delay and a current ventricular interval (indicative of a current time interval between two successive ventricular pacing signals).

The atrial-ventricular delay is the delay at which a ventricular sense signal or pacing signal should ideally follow after an atrial event. An optimized value for the atrial-ventricular delay (in short AV delay) may for example be determined from the averaged measured atrial interval, wherein approaches are well-known to determine an optimal atrial-ventricular delay by for example measuring pulsed wave Doppler of mitral inflow at varying AV delays or obtaining continuous wave Doppler velocity-time integral (VTI) of aortic valve outflow at varying AV delays. The calculated ventricular-atrial delay may be determined by subtracting the value of the atrial-ventricular delay from the ventricular interval.

The calculated ventricular-atrial delay indicates the predicted point in time at which a next atrial event should occur after a prior ventricular pacing or sensing event in case the ventricular rate is correctly synchronized to the atrial sense rate. At the time of occurrence of a ventricular event, i.e., the generation of a ventricular pacing signal or the sensing of an intrinsic ventricular sense signal, a timer is started and is used to measure how much time has elapsed since the last ventricular event. At the time of the next occurrence of an atrial event the time is stored to obtain a time value for a true time of occurrence of an atrial event following the prior ventricular event, wherein the true time of occurrence may be set into relation with the calculated ventricular-atrial delay in order to determine the correction value based on such timing relation.

Moreover, according to an embodiment of the present invention, the processing circuitry is configured to determine a multiplicity of time bins and to evaluate into which time bin $VA_{true}$ falls for determining the correction value (CV).

In one embodiment, based on the calculated ventricular-atrial delay a multiplicity of time bins may be determined, the time bins each being defined by a lower limit and an upper limit and being distributed in time around the calculated ventricular-atrial delay. The time bins are sequentially aligned, one time bin following the next, wherein a central time bin may be defined such that the ventricular-atrial delay falls into that central time bin.

Preferably, according to an embodiment, the processing circuitry is configured to determine a ventricular-atrial (VA) delay feedback value, wherein the VA delay feedback value is proportional to the difference between the calculated ventricular-atrial delay ($VA_{calc}$) and $VA_{true}$, wherein the processing circuitry is configured to calculate the correction value (CV) based on the VA delay feedback value.

Based on such time bins the correction value may be set in order to progressively adapt the ventricular pacing rate to the atrial sense rate. In particular, the processing circuitry may be configured to evaluate into which time bin the true time of occurrence falls for determining the correction value. For this, the true time of occurrence is compared to the limits of each time bin, and if it is found that the true time of occurrence falls between the lower time limit and the upper time limit of a particular time bin, it is identified that the time of occurrence falls into that time bin.

Each time bin herein, in one embodiment, is associated with a specific setting value corresponding to a specific value of adjustment of the ventricular pacing rate. For example, the central time bin into which the ventricular-atrial delay falls may have a setting value of 0, whereas earlier time bins may have progressively increasing setting values and later time bins may have progressively decreasing setting values.

Based on the finding into which time bin the true time of occurrence of a detected atrial event falls, then, the correction value may be set to the setting value of the corresponding time bin. If the true time of occurrence lies in the central time bin into which the ventricular-atrial delay falls the correction value hence becomes 0, such that the ventricular pacing rate is not changed, assuming that a phase match between the ventricular pacing rate and the atrial sense rate is already present. If the true time of occurrence falls into a time bin corresponding to a time range earlier than the calculated ventricular-atrial delay, the correction value assumes a positive value to cause an increase of the ventricular pacing rate, the magnitude of the correction value herein becoming progressively larger the farther the time bin is located from the central time bin. If the true time of occurrence, in contrast, falls into a time bin corresponding to a time range later than the calculated ventricular-atrial delay, the correction value assumes a negative value to cause a decrease in the ventricular pacing rate, the magnitude of the correction value again becoming progressively larger the farther the time bin is located from the central time bin.

By means of the correction value, hence, a progressive adjustment of the ventricular pacing rate is applied. The number of time bins herein may range anywhere between two or three and a significantly larger number of time bins. If, for example, three time bins are used, a central time bin may be associated with a setting value of 0, an earlier time bin preceding the ventricular-atrial delay may be associated with a positive setting value and a later time bin may be associated with a negative setting value.

Generally, by applying the correction value, the processing circuitry is configured to adjust the ventricular pacing rate to synchronize the ventricular pacing rate with the atrial sense rate. Herein, for the adjustment, a first ramping function may be applied in order to progressively adjust the ventricular pacing rate to the atrial sense rate in case the atrial sense rate is suited for controlling a ventricular pacing.

The first ramping function may provide for a linear ramping at a predefined ramping slope. The first ramping function however may also provide for a nonlinear adjustment of the ventricular pacing rate.

In case the atrial sense rate can no longer be determined from the sensing signal picked up by means of the reception device, or in case the atrial sense rate no longer is suited for controlling a ventricular pacing, no pacing according to atrial sense signals can or should be applied. Generally, within a leadless pacemaker device placed in the ventricle it may be difficult to reliably detect atrial signals, as the atrial signals occur in the far field and hence require for example electrical far-field measurements or a sensing of mechanical signals, such as noise signals, acceleration signals or pressure signals stemming from remote locations. Hence, atrial signals may be weak, such that an atrial sense rate may be lost. It in addition is possible that the atrial rhythm is not intact, because atrial contractions occur too slow or too fast. If atrial contractions are too far apart, this may represent a failure in the intrinsic atrial sinus functionality, a development of atrial fibrillation (which may make atrial senses undetectable to the atrial event detection mechanism because of a reduced signal amplitude), or a failure in the detection mechanism. When atrial contractions occur too fast, this may represent an atrial tachycardia or an intrinsic conduction disturbance associated with atrial extra-systoles. If the atrial rate is faster than the ventricle can reliably keep up with, tracking the atrial rate may lead to inefficient ventricular pumping and/or ventricular fatigue, which is to be avoided.

Hence, an atrial tracking involving an adjustment of the ventricular pacing rate to the atrial sense rate should only be initiated—even if an atrial sense rate is detectable—if the atrial sense rate is larger than a lower threshold and smaller than an upper threshold. In this case, the ventricular pacing rate is progressively adapted to the atrial sense rate. If this is not the case, because the atrial sense rate is smaller than the lower threshold and hence too small, or because the atrial sense rate is larger than the upper threshold and hence too large, or if the atrial sense rate is not reliably detectable at all, the atrial tracking mode is, in one embodiment, disabled and no pacing according to atrial sense signals takes place.

In this case, it may be required to adjust the ventricle pacing rate to another pacing strategy, for example to a rate response mechanism allowing for a variation of the ventricular pacing rate according to, e.g., physical activity of a patient. Hence, when disabling the atrial tracking mode, in one embodiment, the processing circuitry may be configured to adjust the ventricular pacing rate to synchronize the ventricular pacing rate with a pacing rate defined by a rate responsive pacing algorithm according to a predefined second ramping function. The second ramping function may then provide for a progressive adjustment of the ventricular pacing rate until it matches the pacing rate controlled and determined by the rate responsive pacing algorithm, i.e., a pacing by taking into account physical signals such as an accelerometer and/or other sensor signals signal indicative of patient activity.

The second ramping function may provide for a linear ramping at a predefined ramping slope. The second ramping function however may also provide for a nonlinear adjustment of the ventricular pacing rate.

The leadless pacemaker device may provide for a continuous ventricular pacing at an adaptive ventricular pacing rate. In another embodiment, the leadless pacemaker device may be configured to provide a pacing in the ventricle only if no intrinsic contraction signals in the ventricle at a suitable timing can be detected. Hence, in one embodiment, the processing circuitry is configured to generate a ventricular pacing signal if no intrinsic ventricular sense signal is detected within a predefined time window following a prior ventricular event. If, instead, an intrinsic ventricular sense signal—over one or multiple cycles—is detected within the predefined time window following the prior ventricular event, no pacing signal is generated and injected, such that in that case no pacing action takes place, but the pacemaker device is in an intrinsic conduction mode without providing an artificial pacing.

The leadless pacemaker device may comprise a housing and an arrangement of electrodes arranged on the housing for emitting pacing signals and, in addition, for receiving reception signals. The housing provides for an encapsulation of the leadless pacemaker device, the leadless pacemaker device including all required components for autarkic operation, such as the processing circuitry, an energy storage such as a battery, electric and electronic circuitry and the like, within the housing. The housing is fluid-tight such that the leadless pacemaker device may be implanted into cardiac tissue and may be kept in cardiac tissue over an extended period of time to provide for a long-time, continuous cardiac pacing operation.

In one aspect, the electrode arrangement comprises a first electrode arranged in the vicinity of a tip of the housing. The first electrode shall come to rest on cardiac tissue in an implanted state of the pacemaker device, such that the first electrode contacts cardiac tissue at a location effective for injecting a stimulating signal into cardiac tissue for provoking a pacing action, in particular a ventricular pacing.

In one aspect, the electrode arrangement comprises a second electrode formed by an electrode ring circumferentially extending about the housing. Alternatively, the second electrode may for example be formed by a patch or another electrically conductive area formed on the housing. The second electrode is placed at a distance from the tip of the housing and hence at a distance from the first electrode arranged at the tip.

In one embodiment, the housing comprises a far end opposite the tip, the electrode arrangement comprising a third electrode arranged on the housing at the far end opposite the tip. The third electrode is operatively connected to the processing circuitry, such that the processing circuitry is enabled to receive and process signals received via the third electrode.

In one aspect, the processing circuitry is configured to process, as a reception signal indicative of atrial activity, a sense signal between the first or the second electrode and the third electrode. Such signal vector arising between the first or second electrode and the third electrode may be referred to as far-field vector, the first or second electrode and the third electrode exhibiting a rather large distance with respect to each other such that a far-field differential signal may be picked up at a reasonable signal-to-noise ratio.

According to an embodiment of the present invention, atrial events (As) and ventricular events (Vs) are sensed via the at least two of the first, second or third electrode.

The reception of atrial signals may take place by electrical measurements using electrodes of the electrode arrangement, such electrodes hence forming part of the reception device for receiving electrical signals. Alternatively or in addition, the reception device may comprise a pressure sensor, a force sensor, a motion sensor or a noise sensor for sensing signals indicative of atrial activity. In such cases atrial activity is not detected based on electrical measurements, but is picked up by signals having a mechanical origin.

At least the object is also addressed by means of a method for operating a leadless pacemaker device configured to provide for an intra-cardiac pacing, the method comprising: generating, using a processing circuitry, ventricular pacing signals for stimulating ventricular tissue, receiving, using a reception device, a sensing signal indicative of an atrial activity, in case a valid atrial sense rate is determined, determine a ventricular pacing rate according to the atrial sense rate based on a calculated atrial-ventricular (AV) delay, generating ventricular pacing signals at the ventricular pacing rate, determine a calculated ventricular-atrial delay (VAcalc) indicative of a time delay at which an atrial event (As) is predicted to occur following a prior ventricular event (Vs), measure a true occurrence of a time delay at which an atrial event (As) occurs following a prior ventricular event (Vs) (VAtrue) and determine a correction value (CV) based on a timing relation between true occurrence of a time delay at which an atrial event (As) occurs following a prior ventricular event (Vs) (VAtrue) and the calculated ventricular-atrial delay (VAcalc), and adjust said ventricular pacing rate based on the correction value (CV).

The advantages and advantageous embodiments described above for the leadless pacemaker device equally apply also to the method, such that it shall be referred to the above.

Additional features, aspects, objects, advantages, and possible applications of the present invention will become apparent from a study of the exemplary embodiments and examples described below, in combination with the Figures and the appended claims.

DESCRIPTION OF THE DRAWINGS

The various features and advantages of the present invention may be more readily understood with reference to the following detailed description and the embodiments shown in the drawings. Herein.

DETAILED DESCRIPTION

Figure 1:
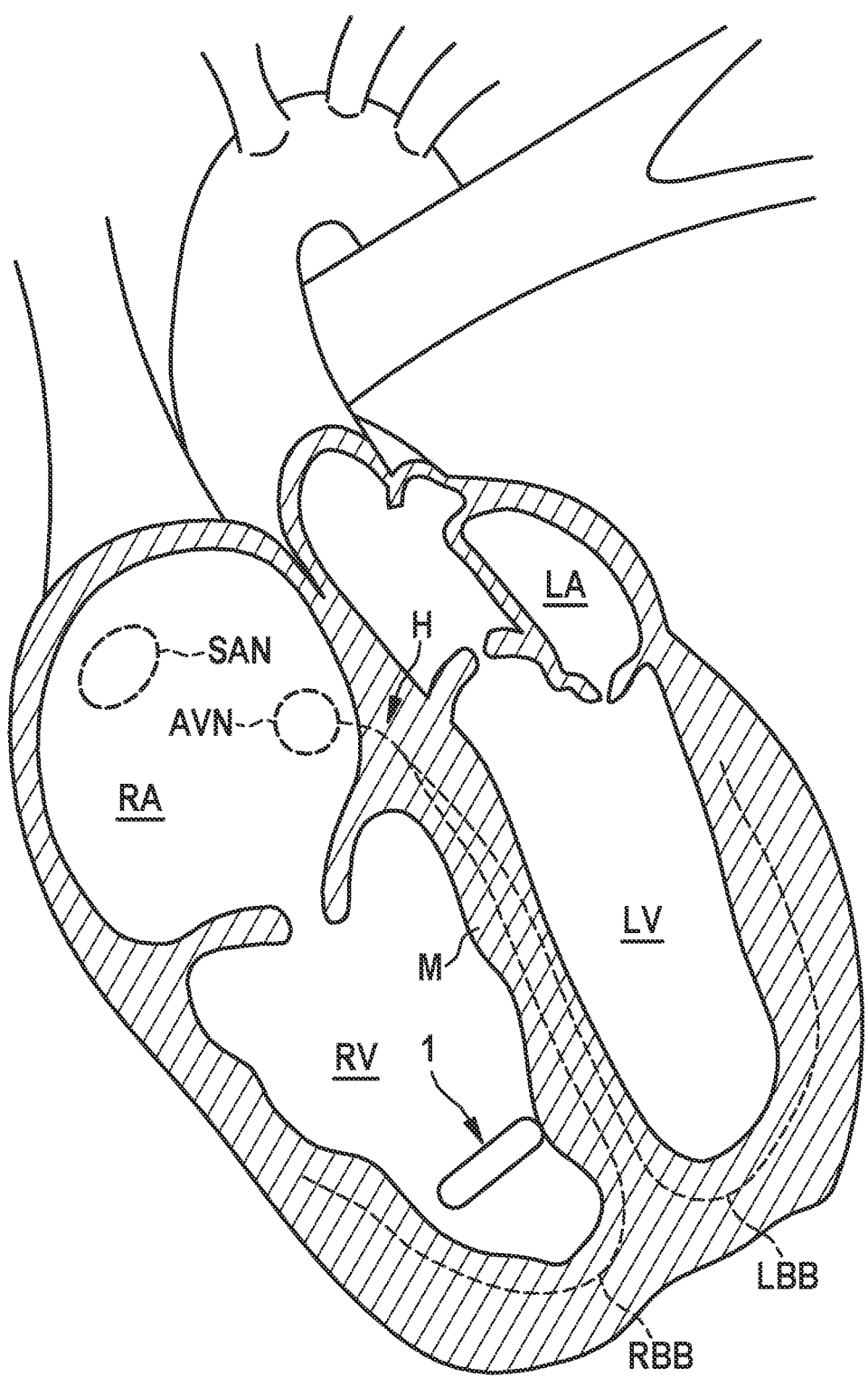
FIG. 1 shows a schematic view of the human heart.

Subsequently, embodiments of the present invention shall be described in detail with reference to the drawings. In the drawings, like reference numerals designate like structural elements.

It is to be noted that the embodiments are not limiting for the present invention, but merely represent illustrative examples.

In the instant invention it is proposed to provide a leadless pacemaker device providing for an intra-cardiac pacing, in particular a ventricular pacing.

FIG. 1 shows, in a schematic drawing, the human heart comprising the right atrium RA, the right ventricle RV, the left atrium LA and the left ventricle LV, the so-called sinoatrial node SAN being located in the wall of the right atrium RA, the sinoatrial node SAN being formed by a group of cells having the ability to spontaneously produce an electrical impulse that travels through the heart's electrical conduction system, thus causing the heart to contract in order to pump blood through the heart. The atrioventricular node AVN serves to coordinate electrical conduction in between the atria and the ventricles and is located at the lower back section of the intra-atrial septum near the opening of the coronary sinus. From the atrioventricular node AVN the so-called HIS bundle H is extending, the HIS bundle H being comprised of heart muscle cells specialized for electrical conduction and forming part of the electrical conduction system for transmitting electrical impulses from the atrioventricular node AVN via the so-called right bundle branch RBB around the right ventricle RV and via the left bundle branch LBB around the left ventricle LV.

In case of a block at the atrioventricular node AVN, the intrinsic electrical conduction system of the heart H may be disrupted, causing a potentially insufficient intrinsic stimulation of ventricular activity, i.e., insufficient or irregular contractions of the right and/or left ventricle RV, LV. In such a case, a pacing of ventricular activity by means of a pacemaker device may be indicated, such pacemaker device stimulating ventricular activity by injecting stimulation energy into intra-cardiac tissue, specifically myocardium M.

Within the instant text, it is proposed to use a leadless cardiac pacemaker device 1, as schematically indicated in FIG. 1, for providing for a ventricular pacing action.

Whereas common leadless pacemaker devices are designed to sense a ventricular activity by receiving electrical signals from the ventricle RV, LV they are placed in, it may be desirable to provide for a pacing action which achieves atrioventricular (AV) synchrony by providing a pacing in the ventricle in synchrony with an intrinsic atrial activity. For such pacing mode, also denoted as atrial tracking, it is required to sense atrial activity and identify atrial events relating to atrial contractions in order to base a ventricular pacing on such atrial events.

Figure 3:
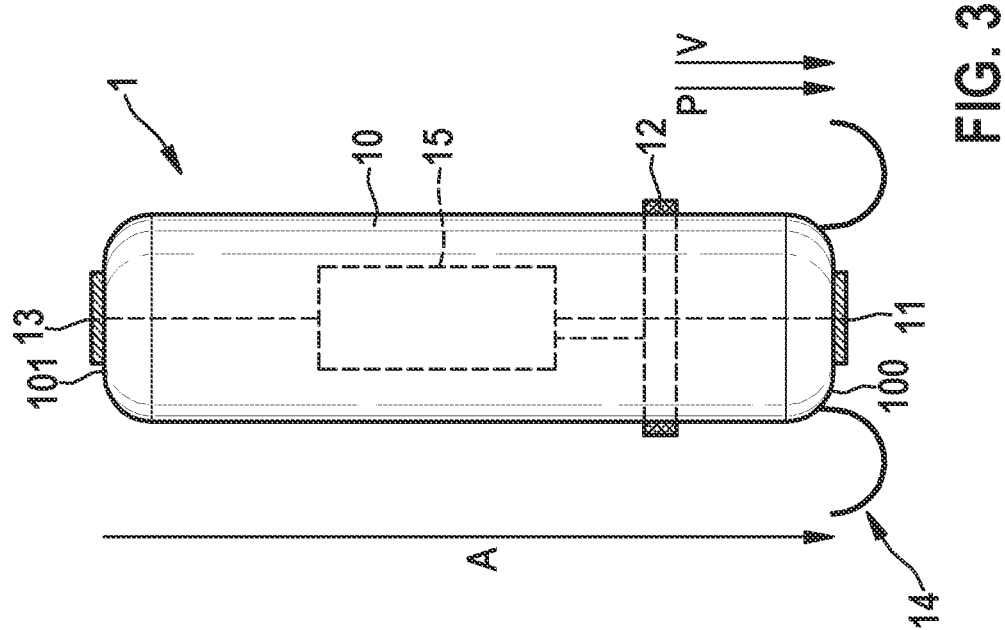
FIG. 3 shows a schematic view of a leadless pacemaker device, indicating signal vectors between different electrodes of the leadless pacemaker device.
Figure 2:
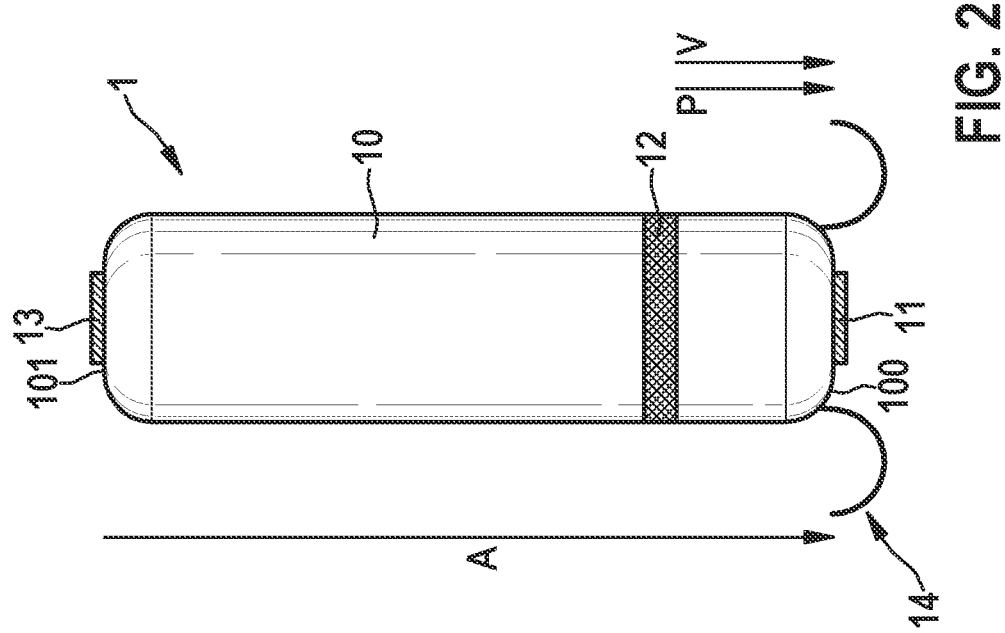
FIG. 2 shows a schematic view of a leadless pacemaker device.

Referring now to FIGS. 2 and 3, in one embodiment a leadless pacemaker device 1 configured to provide for an intra-cardiac pacing, in particular employing an atrial tracking, comprises a housing 10 enclosing electrical and electronic components for operating the leadless pacemaker device 1. In particular, enclosed within the housing 10 is a processing circuitry 15, comprising for example also a communication interface for communicating with an external device, such as a programmer wand. In addition, electrical and electronic components such as an energy storage in the shape of a battery are confined in the housing 10. The housing 10 provides for an encapsulation of components received therein, the housing 10 having the shape of, e.g., a cylindrical shaft having a length of for example a few centimeters.

The leadless pacemaker device 1 is to be implanted on intra-cardiac tissue M first. For this, the leadless pacemaker device 1 comprises, in the region of the tip 100, a fixation device 14 for example in the shape of nitinol wires to engage with intra-cardiac tissue M for fixedly holding the leadless pacemaker device 1 on the tissue in an implanted state.

The leadless pacemaker device 1 does not comprise leads, but receives signals relating to a cardiac activity, in the illustrated embodiment, by means of an electrode arrangement arranged on the housing 10 and also emits stimulation signals by means of such electrode arrangement. In the embodiment of FIGS. 2 and 3, the leadless pacemaker device 1 comprises different electrodes 11, 12, 13 making up the electrode arrangement and serving to emit pacing signals towards intra-cardiac tissue M for providing a pacing and to sense electrical signals indicative of a cardiac activity, in particular indicative of atrial and ventricular contractions.

A first electrode 11 herein is denoted as pacing electrode. The first electrode 11 is placed at a tip 100 of the housing 10 and is configured to engage with cardiac tissue M.

A second electrode 12 serves as a counter-electrode for the first electrode 11, a signal vector P arising between the first electrode 11 and the second electrode 12 providing for a pacing vector for emitting pacing signals towards the intra-cardiac tissue M.

In addition, the second electrode 12 may serve as a sensing electrode for sensing signals, in particular relating to ventricular contractions, a signal vector V arising between the second electrode 12 and the first electrode 11, the signal vector V being denoted as near-field vector.

The second electrode 12 is placed at a distance from the first electrode 11 and for example has the shape of a ring extending circumferentially about the housing 10. The second electrode 12 is for example placed at a distance of about 1 cm from the tip 100 of the housing 10 at which the first electrode 11 is placed.

The leadless pacemaker device 1, in the embodiment of FIGS. 2 and 3, in addition comprises a third electrode 13 placed at a far end 101 of the housing 10, the third electrode 13 serving as a sensing electrode for sensing signals indicative of cardiac activity in the far-field. In particular, a signal vector A arises between the third electrode 13 and the first electrode 11, the signal vector A picking up signals being indicative for example of atrial contractions and being denoted as far-field vector.

The electrodes 11, 12, 13 are in operative connection with the processing circuitry 15, the processing circuitry 15 being configured to cause the first electrode 11 and the second electrode 12 to emit a pacing signal for providing a stimulation at the ventricle. The processing circuitry 15 furthermore is configured to process signals received via the electrodes 11, 12, 13 to provide for a sensing of cardiac activity, in particular atrial and ventricular contractions.

In order to provide for a pacing in the ventricle in which the leadless pacemaker device 1 is placed, in particular to enable a pacing using an atrial tracking, a sensing of atrial activity is required to provide for detected atrial sense markers in order to time a pacing in the ventricle in atrioventricular (AV) synchrony. For this, a far-field signal from in particular the right atrium RA (see FIG. 1) shall be sensed in order to allow for a synchronous pacing in the right ventricle RV by means of the leadless pacemaker device 1 being implanted on intra-cardiac tissue M in the right ventricle RV.

Generally, when a competent sinus rhythm is available, it is preferable to use such sinus rhythm in order to time a ventricular pacing based on the sinus rhythm. Because the pacemaker device 1 is placed in the ventricle, however, signals allowing for a detection of an atrial sense rate being indicative of intrinsic atrial activity may not always be reliably available because received signals may be low in amplitude. In addition, a pacing in the ventricle based on and in synchrony with atrial signals is potentially not suitable if a detected atrial sense rate is too slow or too fast. If atrial events detected based on a signal received from the atrium are too far apart, this may represent a failure of the intrinsic atrial sinus functionality, a development of atrial fibrillation, or a failure in the detection mechanism. If in contrast atrial events are too close together, this may represent an atrial tachycardia or an intrinsic conduction disturbance associated with atrial extrasystoles, in which case the atrial sense rate may be too fast for the ventricle and an atrial tracking should be avoided in order to prevent an inefficient ventricular pumping or ventricular fatigue.

Hence, a switching between an atrial tracking mode and a mode in which the atrial tracking is disabled may be required. In the atrial tracking mode the pacing in the ventricle takes place based on a detected atrial sense rate. In contrast, if the atrial tracking mode is disabled the ventricular pacing takes place by employing another mechanism, such as a rate response mechanism in which the ventricular pacing rate is governed and varies for example in dependence on a detected physical activity of a patient, which may for example be derived from sensor readings such as accelerometer readings or the like.

In general, if the atrial sense rate is too small or too large (i.e., the atrial sense rate is smaller than a lower threshold or larger than an upper threshold), or if no reliable atrial sense rate can be derived from atrial signal, an atrial tracking mode should be disabled. Instead, if an atrial sense rate can be reliably detected because atrial events are continuously received and allow to determine a stable atrial rate, and if in addition the atrial sense rate is in between the lower threshold and the upper threshold, the atrial tracking mode should be enabled.

If the atrial tracking mode is enabled, the ventricular pacing rate should be adapted to the atrial sense rate. Herein, prior to enabling the atrial tracking mode the ventricular pacing rate has been controlled according to another mechanism and hence may substantially differ from the now available atrial sense rate, such that the enabling of the atrial tracking mode involves a control of the ventricular pacing rate such that it now takes account of the atrial sense rate.

In order to avoid a sudden switching from one ventricular pacing rate to another at the time of enabling the atrial tracking mode, it herein is proposed to progressively adjust the ventricular pacing rate such that it is progressively adapted to resemble and follow the atrial sense rate. The progressive adjustment may take into account programmed attack and decay limits such that a slope of the adaption of the ventricular pacing rate does not exceed predefined limits.

In one embodiment, the adjustment of the ventricular pacing rate towards the now available atrial sense rate may follow the principles of a phase-locked loop, the control mechanism being such that a correction value is determined according to a difference between a phase of the atrial sense rate and the current ventricular pacing rate, the correction value being then used to correct the ventricular pacing rate such that it is adjusted towards the atrial sense rate.

Figure 4A:
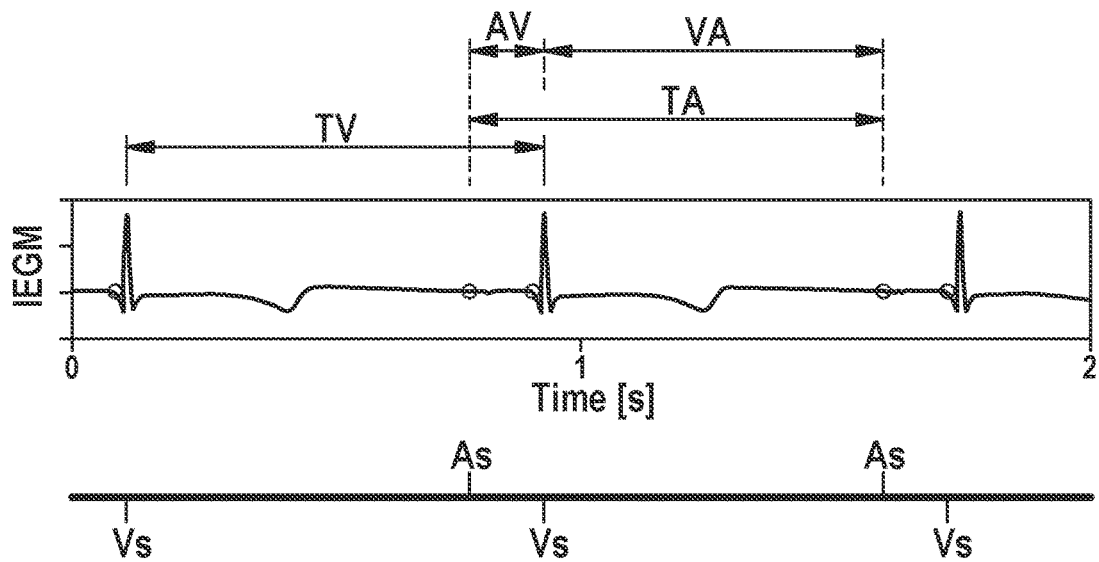
FIG. 4A shows a graphical representation of an intra-cardiac electrogram (IEGM)

In one embodiment, when switching to the atrial tracking mode, an (ideal) atrioventricular delay AV, as illustrated in FIG. 4A according to an example of an intra-cardiac electrogram IEGM, is determined. The calculation of the atrioventricular delay AV may for example make use of an average of an atrial interval TA between two successive atrial events As, the average for example being taken over multiple cycles. The averaged atrioventricular delay AV may then be used, together with the current interval of the ventricular pacing TV, to calculate a ventricular-atrial delay VA being indicative of a predicted time at which an atrial event As should follow a ventricular pacing or sense event Vs (if the ventricular pacing rate and the atrial sense rate are in synchrony.

Figure 4B:
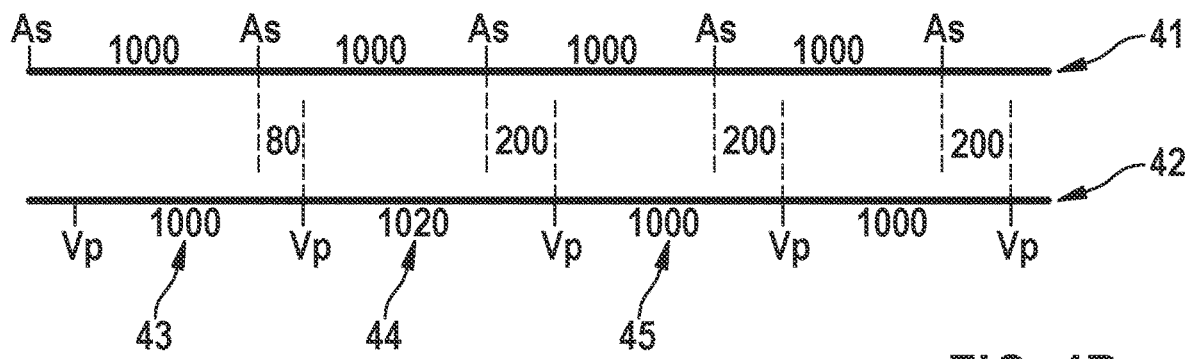
FIG. 4B shows sequential diagram of atrial senses and ventricular paces.

FIG. 4B shows schematically a sequence 41 of atrial sensed events As and the sequence 42 of ventricular paced events Vp according to the atrial sensed events. According to an aspect of the invention, the ventricular pacing rate can be changed to match the atrial sense rate. The atrial pacing rate in sequence 41 of FIG. 4B amounts 60 bpm due to atrial-to-atrial intervals of 1000 ms. Via changing the ventricular pacing rate by a small amount in one cardiac cycle and then returning to the previous rate in the next cycle, the phase relationship of the pace interval and the atrial interval can be adjusted. For example, if the atrial rate is 60 bpm as in sequence 41, and the ventricular pacing rate is 60 ppm, the time duration between the atrial sense and the ventricular pace may be, say, 180 ms (43 in FIG. 4B). If it is desired to adjust the AV delay instead to 200 ms, it is possible to generate a longer ventricular-to-ventricular pacing interval for one cycle (44 in FIG. 4B) and then set the ventricular-to-ventricular interval back to 1000 ms (cycle 45 in FIG. 4B) in order to achieve a temporal shift the Vp with respect to the As. If the AV delay is measured every cycle and compared to the desired delay, such small corrections can be used to continuously keep the AV delay at the proper value even if the atrial rate drifts up and down. A side effect is that the ventricular rate will track the drift in the atrial rate.

Figure 5:
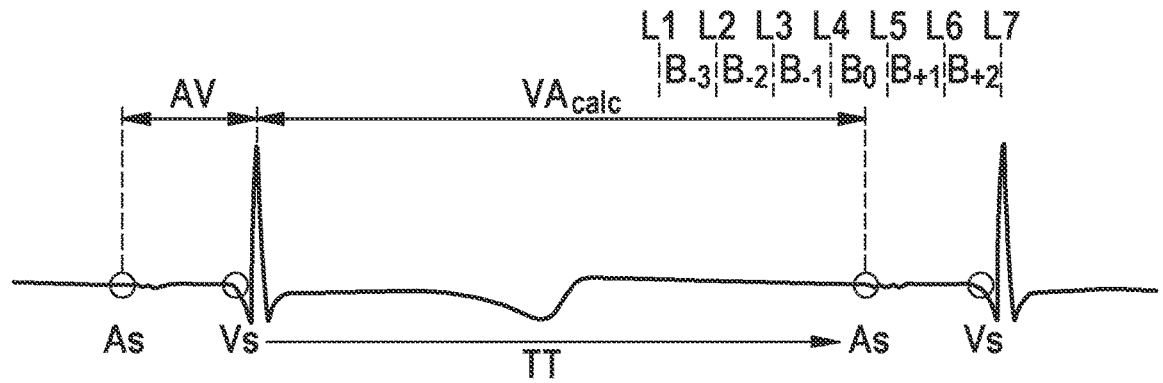
FIG. 5 shows a portion of the intra-cardiac electrogram, illustrating the adjustment of a ventricular rate according to an atrial sense rate.

Based on the calculated ventricular-atrial delay $VA_{calc}$ as indicated in FIG. 5, and based on a measurement of the true time of occurrence of the next atrial event As following a ventricular pacing or sense event Vs, a correction of the ventricular pacing rate may be performed.

In particular, at the time of a ventricular event Vx (which may be a pacing event Vp or which may be an intrinsic ventricular sense event Vs) a timer is started. At the time of the next atrial event As the timer time TT is stored such that the true time of occurrence of the atrial event As following the prior ventricular event Vs is obtained.

The true time of occurrence of the atrial event As may now be compared to the calculated ventricular-atrial delay $VA_{calc}$, and from such comparison a correction value may be determined.

In particular, in one embodiment, as illustrated in FIG. 5 a number of time bins $B_{-3} \ldots B_{+2}$ may be defined, the time bins $B_{-3} \ldots B_{+2}$ being distributed around the calculated ventricular-atrial delay $VA_{calc}$ such that a central time bin $B_0$ contains the calculated ventricular-atrial delay $VA_{calc}$, i.e., the predicted time of occurrence of the atrial event As if the ventricular rate and the atrial sense rate were in synchrony.

Each time bin $B_{-3} \ldots B_{+2}$ herein is bounded by a lower bound $L_1 \ldots L_6$ and an upper bound $L_2 \ldots L_7$, the time bins $B_{-3} \ldots B_{+2}$ having for example identical widths.

Each time bin $B_{-3} \ldots B_{+2}$ is associated with a particular setting value. The central time bin $B_0$ has a setting value of 0. The time bins $B_{-3} \ldots B_{-1}$ preceding the central time bin $B_0$ have a positive setting value, whereas the time bins $B_{+1}$, $B_{+2}$ succeeding the central time bin $B_0$ have a negative setting value.

Based on the measured true time of occurrence of the atrial event As it is now determined into which time bin $B_{-3} \ldots B_{+2}$ the atrial event As falls. The correction value is then set according to the setting value of the corresponding time bin $B_{-3} \ldots B_{+2}$. If the atrial event As falls into the central time bin $B_0$, the correction value hence is set to 0. If the atrial event As falls into a time bin $B_{-3} \ldots B_{-1}$ preceding the central time bin $B_0$, the correction value is set to a positive value according to the specific setting value of the time bin $B_{-3} \ldots B_{-1}$ the true time of occurrence of the atrial event As falls into, wherein the setting values of the time bins $B_{-3} \ldots B_{-1}$ progressively increase the farther away the time bin $B_{-3} \ldots B_{-1}$ is from the central time bin $B_0$. If the atrial event As falls into a time bin $B_{+1}$, $B_{+2}$ succeeding the central time bin $B_0$, the correction value is set to a negative value according to the specific setting value of the time bin $B_{+1}$, $B_{+2}$ the true time of occurrence of the atrial event As falls into, the magnitude of the setting value of the time bin $B_{+1}$, $B_{+2}$ again increasing the farther the time bin $B_{+1}$, $B_{+2}$ is away from the central time bin $B_0$.

A positive correction value causes an increase in the ventricular pacing rate such that the ventricular pacing takes place at a faster rate. A negative correction value causes a reduction in the ventricular pacing rate such that the ventricular pacing is slowed down. In the instant embodiment, because the correction value is progressively set based on a difference between the ventricular rate and the atrial sense rate, determined by comparing a true time of occur of occurrence of an atrial event As (following a prior ventricular event Vs) with a predicted time of occurrence (represented by the calculated ventricular-atrial delay $VA_{calc}$), the ventricular pacing rate is progressively changed until it has converged to the atrial sense rate, hence avoiding a sudden switching between distinct ventricular pacing rates when switching from one pacing mode to another.

Figure 6:
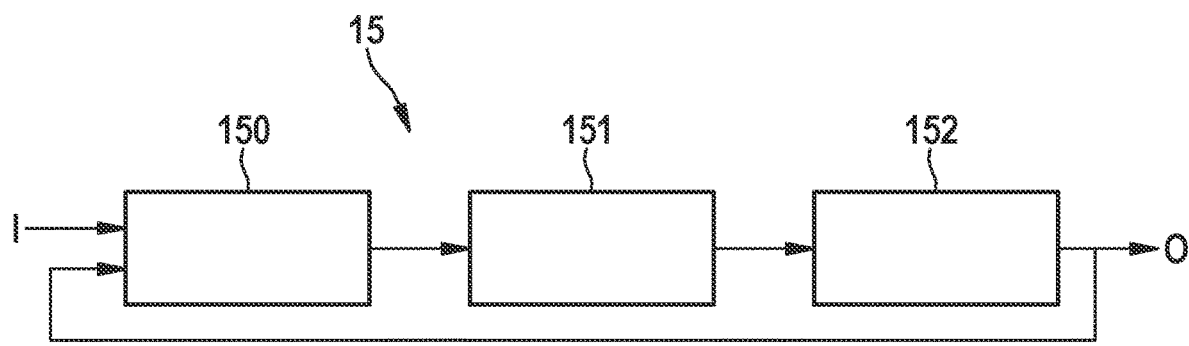
FIG. 6 illustrates a schematic of an adjustment mechanism for adjusting the ventricular pacing rate.

The principle of adjusting the ventricular pacing rate when enabling the atrial tracking mode (and likewise when disabling the atrial tracking mode causing a switch to another pacing mode) may be compared with a phase-locked loop technique, as it is generally illustrated in FIG. 6.

Within such technique, an input I, namely in the instant case the atrial sense rate, is compared in a comparator 150 to an output rate O, in the instant case the ventricular pacing rate. The comparator 150 in particular determines a difference in the phase between the input rate I, namely the atrial sense rate, and the output rate O, namely the ventricular pacing rate, and provides the difference towards a filtering unit 151 which may provide for a filtering in order to improve stability of the control mechanism. The filtered difference is then forwarded to an adjustment unit 152 which, according to the difference, determines a correction value for correcting the output rate O, namely the ventricular pacing rate, and adjusts the output rate O accordingly. The now corrected output rate O, namely the ventricular pacing rate, is fed back to the input, such that a feedback mechanism is provided for progressively adjusting the output rate O, namely the ventricular pacing rate, according to an input rate I, namely the atrial sense rate.

Figure 7:
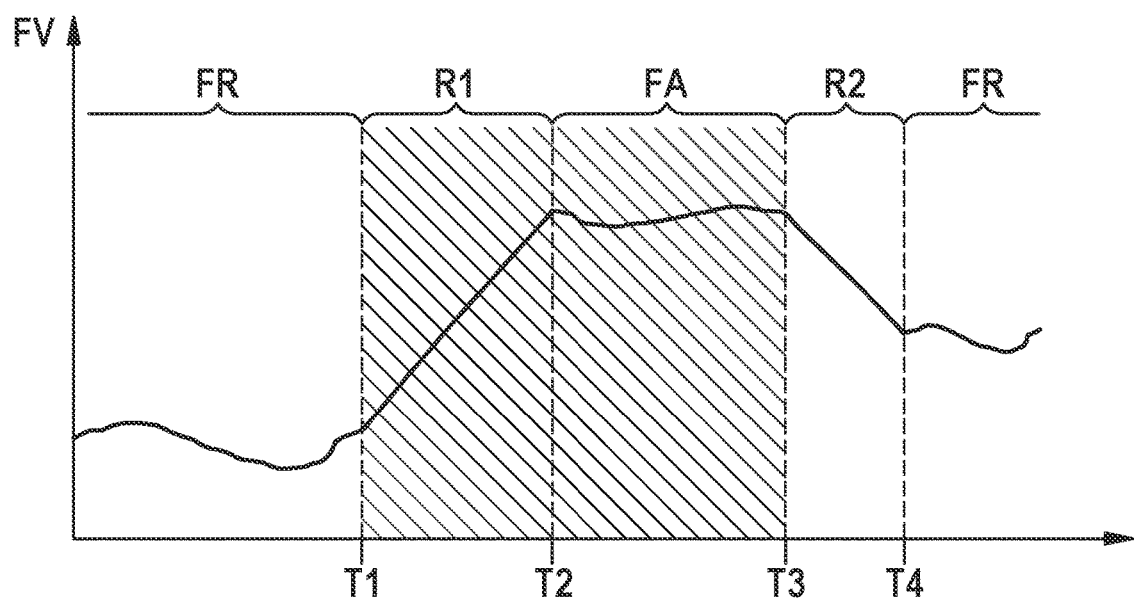
FIG. 7 illustrates an adjustment of the ventricular rate when switching between different pacing modes.

The adjustment of the ventricular pacing rate hence takes place according to predefined attack and decay limits for a rate of change such that the change in the ventricular pacing rate takes place progressively. This is illustrated in FIG. 7.

Herein, prior to a time T1 the ventricular pacing rate is controlled according to a pacing mechanism other than an atrial tracking. The ventricular pacing rate may, for example, be controlled according to a rate response mechanism in which the ventricular pacing rate is varied according to a physical activity of a patient to assume a rate response rate FR, such that the ventricular pacing rate is reduced in times of inactivity, for example, during sleep, and is increased in times of heavy activity, for example during heavy physical exercise.

Prior to time T1 no atrial sense rate is available or suitable for pacing. At time T1 a suitable atrial sense rate FA becomes available, such that the pacemaker device 1 switches to an atrial tracking mode in which the ventricular pacing rate is controlled according to a detected atrial sense rate FA.

In a first phase, herein, between times T1 and T2 the ventricular pacing rate is ramped up according to a ramping function R1 until it is in synchrony with the atrial sense rate FA at time T2 and from that time on is controlled in synchrony with the atrial sense rate FA. The ramping function R1 is defined by the progressive adjustment of the ventricular rate using an iterative application of suitable correction values as described, for one embodiment, above.

At time T3 a suitable atrial sense rate no longer is available, either because of an undersensing of atrial signals or because the atrial sense rate has become too small or too high. In that case the pacemaker device 1 switches back to another pacing mode, for example to a pacing mode making use of a rate response mechanism. Again, in order to avoid a sudden switching of the ventricular pacing rate, the ventricular pacing rate is progressively adapted by applying a ramping function R2 until it has converged towards the rate response rate FR.

For the switching back to the rate response rate FR a similar mechanism as for the switching to synchronize with the atrial sense rate may be applied.

The ventricular pacing may be continuous such that a pacing signal is generated and injected into cardiac tissue independent of intrinsic ventricular activity. Alternatively, intrinsic signals may be sensed and taken into account in order to avoid a ventricular pacing in case intrinsic ventricular signals are present. For this, at each ventricular event Vs, may it be a ventricular pacing event or a ventricular sense event due to intrinsic ventricular activity, a ventricular pacing rate timer may be started, the timer defining a maximum time until which an intrinsic ventricular event must occur in order to avoid a ventricular pacing signal. If the timer has not timed out when an intrinsic ventricular event Vs is detected, the generation of a ventricular pacing signal is skipped. If the timer does timeout, a ventricular pacing signal is generated and injected.

As illustrated above according to FIGS. 2 and 3, for detecting atrial signals to derive an atrial sense rate, beneficially a far-field vector in between electrodes 11, 13 being farthest away on the housing 10 of the pacemaker device 1 is used. Such large vector is preferred in order to accentuate variations in the electromagnetic field paths from the right atrial tissue to the electrodes 11, 13, allowing for a detection of a differential signal indicative of atrial activity.

The measured signal should be filtered in order to differentiate atrial signals from other signals, in particular ventricular signals, and a blanking mechanism may in addition be employed to blank out signals not related to atrial activity.

Figure 8A:
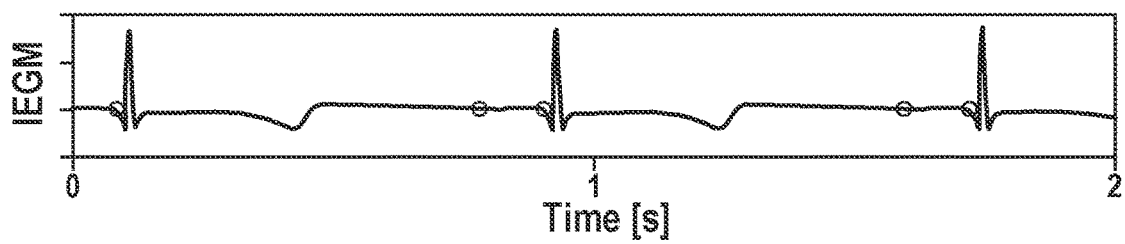
FIG. 8A shows an intra-cardiac electrogram, prior to processing.
Figure 8B:
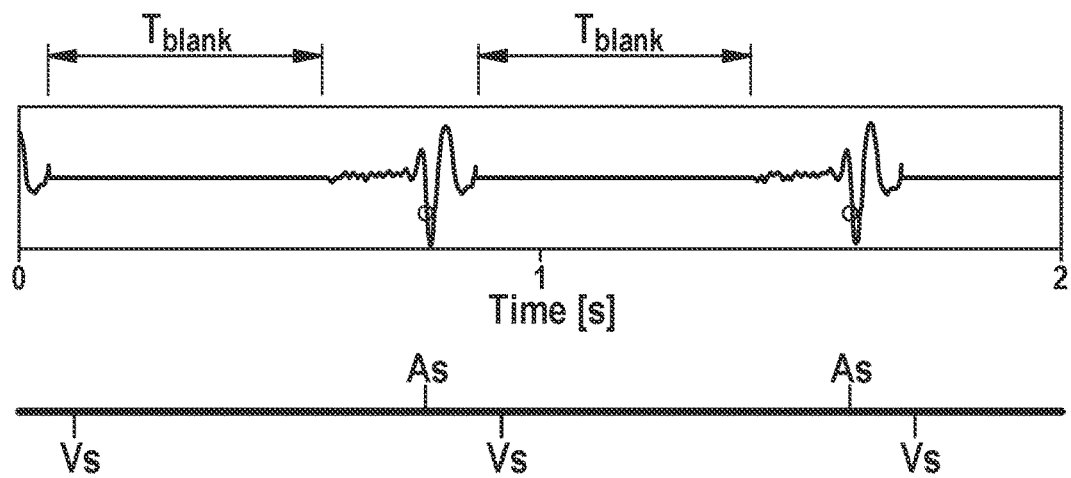
FIG. 8B shows a processed signal stream derived from the intra-cardiac electrogram to derive atrial events.

This is illustrated, in an example, in FIGS. 8A and 8B, illustrating an intra-cardiac electrogram IEGM measured in the ventricle prior to filtering and blanking (FIG. 8A) and after filtering and blanking (FIG. 8B). In particular, a blanking window $T_{blank}$ may be employed to blank out such periods of the signals which may relate to activity in the heart other than atrial activity.

The processed and filtered signal is then used to determine atrial events As.

Figure 9:
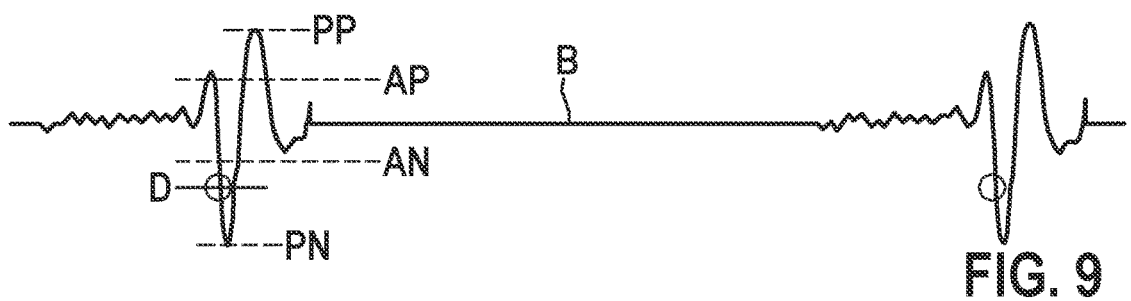
FIG. 9 shows a portion of the processed signal to determine characteristic values from that signal for the determination of an atrial event.

Atrial events As may in particular be determined by employing a processor or state-machine logic. In particular, for determining an atrial event Vs a signal may be analyzed, as illustrated in FIG. 9, for determining a maximum positive peak PP, a maximum negative peak PN, an average value AP of positive signal portions above a baseline B, and an average value AN of negative portions below the baseline B. An atrial event As may then for example be determined according to a crossing of a threshold D, wherein one or multiple thresholds may be employed, for example a positive threshold and a negative threshold, the thresholds being for example calculated according to the characteristics determined from the processed signal.

Generally, if intrinsic ventricular activity is present, beneficially such intrinsic signals should not be interrupted by an artificial pacing, dependent on however whether the intrinsic ventricular activity is in synchrony with atrial activity. If a synchronous intrinsic ventricular activity is present, the pacemaker device 1 should be operated in an intrinsic conduction mode in which the heart operates naturally making use of its intrinsic conduction mechanism.

Figure 10:
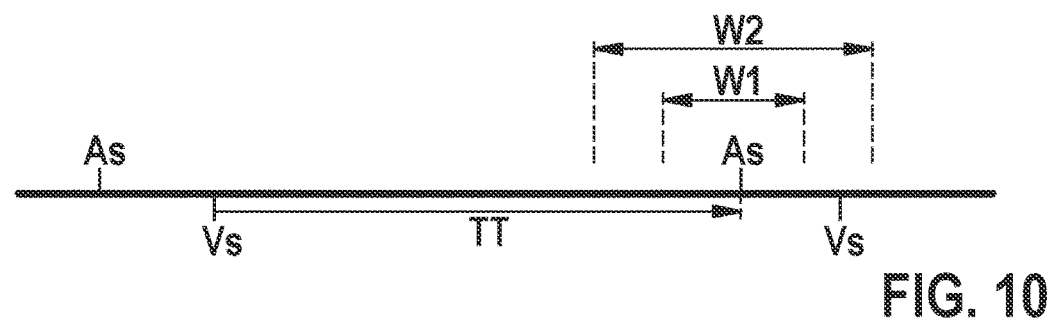
FIG. 10 shows the establishment of windows around a calculated ventricular-atrial delay for determining whether a ventricular rate is in synchrony with an atrial sense rate.

In the intrinsic conduction mode the pacemaker device 1 observes ventricular activity in particular with respect to its synchrony with atrial activity. For this, time windows W1, W2 as illustrated in FIG. 10 may be established in order to monitor the time duration between a ventricular event Vs and a following atrial event As.

The windows W1, W2 herein may be established based on a calculated ventricular-atrial delay $VA_{calc}$ as referred to above (see in particular FIGS. 4 and 5 and the corresponding description), the calculated ventricular-atrial delay $VA_{calc}$ indicating the time at which an atrial event As should follow a prior ventricular event Vs if the ventricular rate and the atrial rate are in synchrony.

The windows W1, W2 in particular may be centered about the ventricular-atrial delay $VA_{calc}$, wherein at each intrinsic ventricular event Vs a timer is started and a true time of occurrence of an atrial event As (timer time TT) is determined and stored. If the true time of occurrence of the atrial event As falls into the inner window W1, it is assumed that the ventricular rate and the atrial rate are in synchrony, and the pacemaker device remains in the intrinsic conduction mode, hence not providing any artificial pacing.

If the true time of occurrence of the atrial event As, instead, is outside the inner window W1, but still falls within the outer, wider window W2 (also referred to as drift window) it is assumed that atrioventricular synchrony is lost. The processing circuitry 15 of the pacemaker device 1 hence switches into an atrial tracking mode and controls the ventricular rate by generating and injecting pacing signals. For adjusting the ventricular pacing rate to the atrial sense rate, herein, an algorithm as described above according to FIG. 5 may be employed, hence adjusting the ventricular pacing rate analogously to a phase-locked loop control.

If a predetermined number of consecutive ventricular senses occurs in synchrony with the atrial rate, the control logic may switch back to the intrinsic conduction mode.

If within the windows W1, W2 no atrial events As occur, the control logic of the processing circuitry 15 may switch to a searching mode in which it is searched for atrial events As. Within such searching mode the ventricular rate may be controlled according to another pacing mechanism, such as a rate response mechanism, wherein the ventricular pacing rate may be progressively adjusted to approach the rate as controlled by the rate response mechanism.

A search for atrial events As is initiated when the processing circuitry 15 is in the searching mode. In the searching mode the processing circuitry 15 may analyze an intra-cardiac electrogram reading for potential atrial events and may determine characteristic values such as peak values and average values to evaluate potential candidates for atrial events. Bandpass filters may be employed to cover a frequency range of a supported atrial sensing, wherein frequencies may be sorted into a continuous range of filter bins. A digital data stream which is analyzed by the processing circuitry may feed into such filter bins, wherein threshold detectors may be enabled at the output of each filter (except the filter that covers the rate interval that corresponds with the current ventricular rate). The threshold value employed by the threshold detectors may be a common value that can be controlled by the search algorithm. The threshold value herein may be raised or lowered until just one detector is active during a predetermined number of consecutive ventricular cycles. An interval associated with this detector is then used to reload a ventricular timer at each ventricular event Vs. If this results in stable candidate atrial events within the calculated ventricular-atrial delay $VA_{calc}$, it is assumed that an atrial sense rate now again is picked up and the control logic may switch back to the intrinsic conduction mode or to the atrial tracking mode. If in contrast within the calculated ventricular-atrial delay $VA_{calc}$ no stable candidate atrial event As is detected, the search circuitry may be disabled to save power, and pacing continues for example according to a rate response mechanism.

If a search has not been successful in identifying stable atrial events As, a predetermined search delay may be initiated for temporarily pause searching. The control logic, during the search delay, uses an adaptive rate according to the rate response mechanism to reload the ventricular timer, and at the end of the search delay the search circuitry may be enabled again to perform another search. This may repeat indefinitely as long as no stable candidate atrial events As are detected and hence no reliable atrial sense rate is picked up.

Between searches, the control logic may monitor for consistent candidate atrial events As within the ventricular-atrial delay window (window W1 in FIG. 10), and if stable atrial events As are detected, the control logic switches back to the intrinsic conduction mode.

Figure 11:
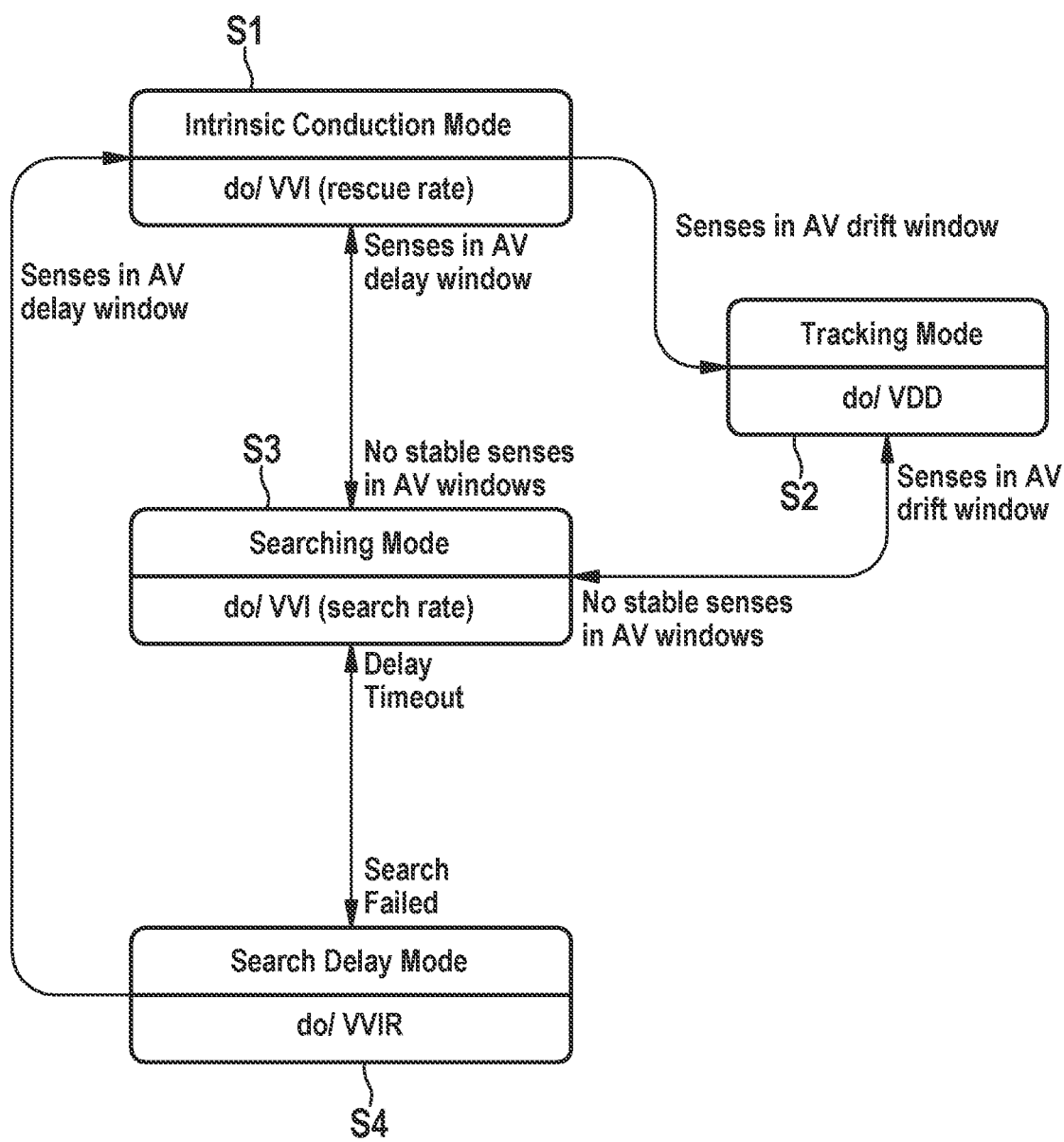
FIG. 11 shows a flow diagram for switching between different modes of a pacemaker device.

The switching between different modes is illustrated, according to an embodiment, in FIG. 11. If an atrial sense rate is detected and is in synchrony with a ventricular rate of intrinsic ventricular event Vs, the pacemaker device 1 is in the intrinsic conduction mode S1. If synchrony is lost because the ventricular rate and the atrial rate drift out of synchrony, the pacemaker device 1 switches into the tracking mode S2. If either in the intrinsic conduction mode S1 or the tracking mode S2 no stable atrial senses allowing for a detection of an atrial sense rate are available, the device switches into the searching mode S3. If a search is performed, but is not successful in identifying stable atrial events As, the device may switch into a delay mode S4 in which a search is paused and a search circuitry is powered off an order to save energy, until at the end of the search delay the device switches back to the searching mode S3. If again a reliable atrial sense rate in synchrony with a ventricular rate is detected, the device switches back to the intrinsic conduction mode S1 (or, if the atrial sense rate is not in synchrony with the ventricular rate, to the tracking mode S2).

Figure 12:
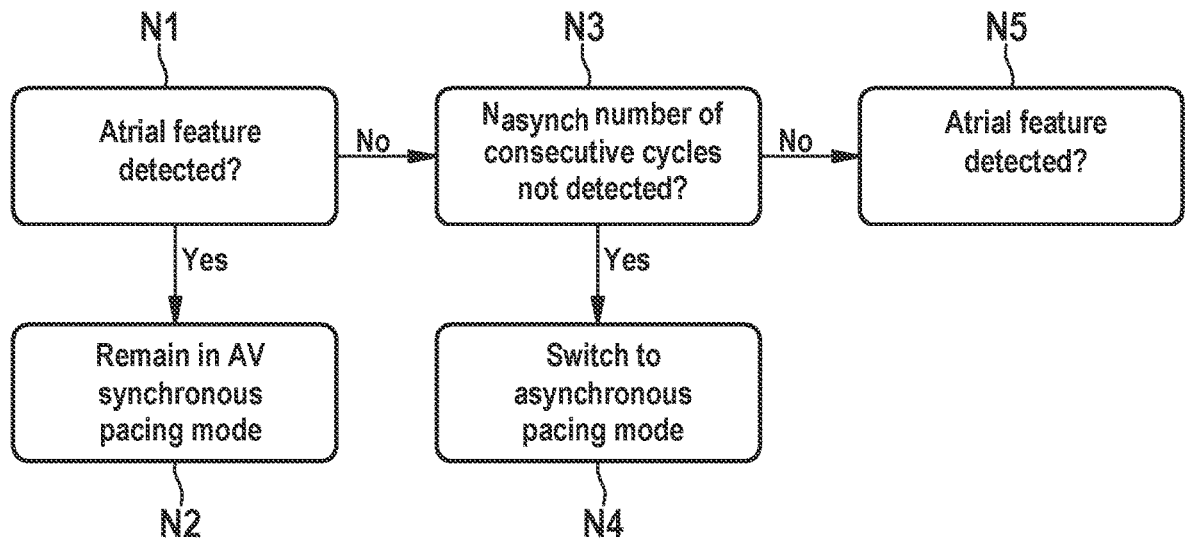
FIG. 12 shows a flow diagram for switching from a synchronous mode to an asynchronous mode.
Figure 13:
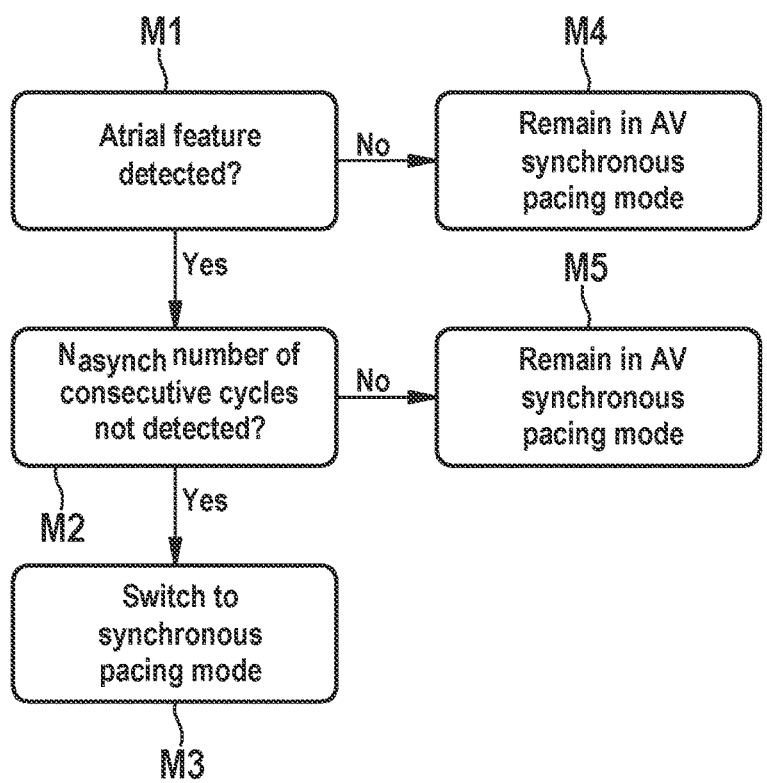
FIG. 13 shows a flow diagram for switching from an asynchronous mode to a synchronous mode.

A general schematic of the switching between an atrio-ventricular synchronous mode, involving an atrial tracking, and an asynchronous mode is illustrated in FIGS. 12 and 13.

In the synchronous mode an atrial tracking is employed, the ventricular pacing rate hence following the intrinsic atrial sense rate. If, in the synchronous mode (state N1 in FIG. 12), atrial features are detected and an atrial sense rate hence is reliably picked up, the device remains in the synchronous mode (state N2). If instead no atrial event As is detected, it may be checked whether an atrial event As cannot be detected for a predetermined number of cycles $N_{asynch}$, for example 10 consecutive cycles. If indeed no atrial event As can be detected for such predetermined number of cycles $N_{asynch}$ (state N3), it is switched to the asynchronous pacing mode (state N4). If atrial events As are again picked up prior to reaching the predefined number of consecutive cycles $N_{asynch}$ in state N3, the device remains in the synchronous mode (state N5).

If the device is in the asynchronous mode (state M1 as illustrated in FIG. 13), it is checked whether an atrial feature As is detected. If this is the case, it may be checked if atrial events As can be stably detected for a predetermined number of cycles $N_{synch}$, for example 10 cycles (state M2). If this is the case, it is switched to the synchronous mode (state M3).

If in state M1 no atrial features are detected, the device remains in the asynchronous pacing mode (state M4). If in state M2 stable atrial events As cannot be detected for the predetermined number of cycles $N_{synch}$, the device also remains in the asynchronous pacing mode (state M5).

The predetermined number of cycles $N_{asynch}$ for switching to the asynchronous mode (state N3 in FIG. 12) and the predetermined number of cycles $N_{synch}$ for switching from the asynchronous mode to the synchronous mode (state M2 in FIG. 13) may be equal or may differ from each other. The predetermined number of cycles $N_{asynch}$, $N_{synch}$ may be for example 10, but may also be larger or smaller.

Algorithms and procedures to control a pacing rate and to switch from one mode to another are implemented in the processing circuitry 15 of the pacemaker device 1 for example by software run on one or multiple suitable processors.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1 Leadless pacemaker device
10 Housing
100 Tip
101 Far end
11 First electrode (pacing electrode)
12 Second electrode (pacing ring)
13 Third electrode
14 Fixation device
15 Processing circuitry
150 Comparator
151 Filtering unit
152 Adjustment unit
A Atrial vector
AN Negative average
AP Positive average
As Atrial event
AV Atrial-ventricular delay
AVN Atrioventricular node
B Baseline
$B_0$, $B_{-1}$, $B_{-2}$, $B_{-3}$, $B_{+1}$, $B_{+2}$ Time bin
CV Correction value
D Threshold value
FA Atrial rate
FR Rate response rate
FV Ventricular rate
H HIS bundle
L1-L7 Limit
LA Left atrium
LBB Left bundle branch
LV Left ventricle
M Intra-cardiac tissue (myocardium)
P Pacing vector
PN Negative peak value
PP Positive peak value
R1, R2 Ramping function
RA Right atrium
RBB Right bundle branch
RV Right ventricle
S1-S4 Modes
T1-T4 Time
TA Atrial interval
TV Ventricular interval
$T_{blank}$ Blanking window
TT Timer time
SAN Sinoatrial node V Ventricular vector
VA Ventricular-atrial delay
$VA_{calc}$ Calculated ventricular-atrial delay
Vs Ventricular event
W1, W2 Window

What is claimed is:

1. A leadless pacemaker device configured to provide for an intra-cardiac pacing, the leadless pacemaker device comprising:
a processing circuitry configured to generate ventricular pacing signals for stimulating ventricular tissue, and
a reception device for receiving a sensing signal indicative of an atrial activity, wherein the processing circuitry is configured to detect an atrial event derived from said sensing signal, wherein the atrial event is a valid atrial sense event, where a series of atrial events lie within a range for a normal atrial rate, and/or when the atrial rate variability is within a certain range indicating a regular atrial rhythm,
wherein in case a valid atrial sense event is detected, the processing circuitry is further configured to:
determine a ventricular pacing event according to the atrial event based on a calculated atrial-ventricular (AV) delay,
determine a calculated ventricular-atrial delay ($VA_{calc}$) indicative of a time delay at which an atrial event (As) is predicted to occur following a prior ventricular event (Vs),
measure a true occurrence of a time delay ($VA_{true}$) at which an atrial event (As) occurs following a prior ventricular event (Vs) and determine a correction value (CV) based on a timing relation between $VA_{true}$ and the calculated ventricular-atrial delay ($VA_{calc}$), and
adjust said ventricular pacing timing based on the correction value (CV).

2. The leadless pacemaker device of claim 1, wherein in case no valid atrial sense event is detected, the processing circuitry is configured to determine a ventricular pacing event based on a calculated ventricular pacing event.

3. The leadless pacemaker device of claim 1, wherein the processing circuitry is configured to determine the calculated ventricular-atrial delay ($VA_{calc}$) based on a calculated atrial-ventricular delay (AV) and a current ventricular interval (TV) indicative of a time interval between two successive ventricular pacing signals.

4. The leadless pacemaker device of claim 1, wherein the processing circuitry is configured to determine a multiplicity of time bins ($B_0$, $B_{-1}$, $B_2$, $B_{-3}$, $B_{+1}$, $B_{+2}$) and to evaluate into which time bin ($B_0$, $B_{-1}$, $B_{-2}$, $B_{-3}$, $B_{+1}$, $B_{+2}$) $VA_{true}$ falls for determining the correction value (CV).

5. The leadless pacemaker device of claim 4, wherein each time bin ($B_0$, $B_{-1}$, $B_{-2}$, $B_{-3}$, $B_{+1}$, $B_{+2}$) is defined by a lower time limit and an upper limit.

6. The leadless pacemaker device of claim 4, wherein each time bin ($B_0$, $B_{-1}$, $B_{-2}$, $B_{-3}$, $B_{+1}$, $B_{+2}$) is associated with a specific setting value, wherein the processing circuitry is configured to set the correction value (CV) using the setting value of the time bin ($B_0$, $B_{-1}$, $B_{-2}$, $B_{-3}$, $B_{+1}$, $B_{+2}$) $VA_{true}$ falls in.

7. The leadless pacemaker device claim 4, wherein the processing circuitry is configured to increase a ventricular pacing rate, determined by a multitude of ventricular events, if $VA_{true}$ falls into a time bin ($B_0$, $B_{-1}$, $B_{-2}$, $B_{-3}$, $B_{+1}$, $B_{+2}$) preceding the end of the calculated ventricular-atrial delay ($VA_{calc}$), and to decrease the ventricular pacing rate if the true time of occurrence falls into a time bin ($B_0$, $B_{-1}$, $B_{-2}$, $B_{-3}$, $B_{+1}$, $B_{+2}$) succeeding the end of the calculated ventricular-atrial delay ($VA_{calc}$).

8. The leadless pacemaker device of claim 1, wherein the processing circuitry is configured to determine a VA delay feedback value, wherein the VA delay feedback value is proportional to the difference between the calculated ventricular-atrial delay ($VA_{calc}$) and $VA_{true}$, wherein the processing circuitry is configured to calculate the correction value (CV) based on the VA delay feedback value.

9. The leadless pacemaker device of claim 7, wherein the processing circuitry is configured to adjust said ventricular pacing rate to synchronize with an atrial sense rate, determined by a multitude of atrial events, according to a predefined first ramping function (R1) when the atrial sense rate is suited for pacing.

10. The leadless pacemaker device of claim 9, wherein the processing circuitry is configured to adjust said ventricular pacing rate to synchronize with a pacing rate defined by a rate responsive pacing algorithm according to a predefined second ramping function (R2) when the atrial sense rate is not suited for pacing.

11. The leadless pacemaker device of claim 1, wherein the processing circuitry is configured to generate a ventricular pacing signal if no intrinsic ventricular sense signal is detected within a predefined time window following a prior ventricular event (Vs).

12. The leadless pacemaker device of claim 1, wherein the reception device comprises at least two electrodes for receiving a sensing signal indicative of atrial activity.

13. The leadless pacemaker device of claim 12, comprising a housing having a tip and a far end, wherein one electrode is arranged in the vicinity of the tip and another electrode is arranged in the vicinity of the far end.

14. A method for operating a leadless pacemaker device configured to provide for an intra-cardiac pacing, comprising:
generating, using a processing circuitry, at least one ventricular pacing signals for stimulating ventricular tissue,
receiving, using a reception device, a sensing signal indicative of an atrial activity,
detecting an atrial event (As) derived from said sensing signal, wherein the atrial event is a valid atrial sense event, where a series of atrial sense events lie within a range for a normal atrial rate, and/or when the atrial rate variability is within a certain range indicating a regular atrial rhythm,
in case a valid atrial sense event is detected,
determine a ventricular pacing event according to the atrial event based on a calculated atrial-ventricular (AV) delay,
determine a calculated ventricular-atrial delay ($VA_{calc}$) indicative of a time delay at which an atrial event (As) is predicted to occur following a prior ventricular event (Vs),
measure a true occurrence of a time delay ($VA_{true}$) at which an atrial event (As) occurs following a prior ventricular event (Vs) and determine a correction value (CV) based on a timing relation between true occurrence of a time delay at which an atrial event (As) occurs following a prior ventricular event (Vs) ($VA_{true}$) and the calculated ventricular-atrial delay ($VA_{calc}$);

adjust said ventricular pacing timing based on the correction value (CV).

* * * * *